United States Patent
Tanaka et al.

(10) Patent No.: US 11,260,124 B2
(45) Date of Patent: Mar. 1, 2022

(54) ANTI-HUMAN NGF ANTIBODY FAB FRAGMENT AND METHODS FOR TREATING POSTOPERATIVE PAIN RELATED TO NGF

(71) Applicant: Astellas Pharma Inc., Chuo-ku (JP)

(72) Inventors: Hirotsugu Tanaka, Tokyo (JP); Hirotada Fujita, Tokyo (JP); Toshiaki Aoki, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/575,969

(22) PCT Filed: May 20, 2016

(86) PCT No.: PCT/JP2016/065099
§ 371 (c)(1),
(2) Date: Nov. 21, 2017

(87) PCT Pub. No.: WO2016/190263
PCT Pub. Date: Dec. 1, 2016

(65) Prior Publication Data
US 2018/0147281 A1    May 31, 2018

(30) Foreign Application Priority Data

May 22, 2015 (JP) .............................. JP2015-104806

(51) Int. Cl.
| | | |
|---|---|---|
| *A61K 39/395* | (2006.01) | |
| *C07K 16/00* | (2006.01) | |
| *C07K 16/18* | (2006.01) | |
| *A61K 39/00* | (2006.01) | |
| *C12N 15/06* | (2006.01) | |
| *C12N 15/00* | (2006.01) | |
| *C12N 15/09* | (2006.01) | |
| *C12N 15/10* | (2006.01) | |
| *C12P 21/00* | (2006.01) | |
| *G01N 33/53* | (2006.01) | |
| *G01N 33/567* | (2006.01) | |
| *C07K 16/22* | (2006.01) | |
| *C12N 5/10* | (2006.01) | |
| *C07K 16/28* | (2006.01) | |
| *A61P 25/00* | (2006.01) | |
| *A61P 25/02* | (2006.01) | |
| *A61P 27/00* | (2006.01) | |
| *A61P 25/04* | (2006.01) | |
| *A61P 29/00* | (2006.01) | |

(52) U.S. Cl.
CPC ........ *A61K 39/39533* (2013.01); *A61P 25/00* (2018.01); *A61P 25/02* (2018.01); *A61P 25/04* (2018.01); *A61P 27/00* (2018.01); *A61P 29/00* (2018.01); *C07K 16/22* (2013.01); *C07K 16/2875* (2013.01); *C12N 5/10* (2013.01); *C12N 15/09* (2013.01); *A61K 2039/505* (2013.01); *C07K 2317/40* (2013.01); *C07K 2317/55* (2013.01); *C07K 2317/56* (2013.01); *C07K 2317/76* (2013.01); *C07K 2317/92* (2013.01); *C07K 2317/94* (2013.01)

(58) Field of Classification Search
CPC ............ A61K 39/39533; A61K 39/395; A61K 2039/505; A61P 25/04; A61P 29/00; C07K 16/22; C07K 2317/51; C07K 2317/515; C07K 2317/565; C07K 2317/16; C07K 2327/52; C07K 2317/567; C07K 14/48; C07K 2317/56; C07K 2317/622; C07K 2317/33; C07K 2317/92; C07K 2317/41; C12N 15/09; G01N 33/6854; G01N 33/6896; C07D 413/12; C07D 417/12; C07D 403/12; C07D 401/12; C07D 405/12
See application file for complete search history.

(56) References Cited

U.S. PATENT DOCUMENTS

| | | | |
|---|---|---|---|
| 5,527,358 A | 6/1996 | Mehmanesh et al. | |
| 8,435,523 B2 | 5/2013 | Powell et al. | |
| 9,315,571 B2* | 4/2016 | Franks | C07K 16/22 |
| 9,328,164 B2* | 5/2016 | Gearing | C07K 16/22 |
| 2012/0156255 A1 | 6/2012 | Singh et al. | |

(Continued)

FOREIGN PATENT DOCUMENTS

| | | | | |
|---|---|---|---|---|
| EP | 2743348 | * | 6/2014 | ............. C12N 15/09 |
| JP | H 09-508039 | | 8/1997 | |

(Continued)

OTHER PUBLICATIONS

WO2013022083—English translated version, Kamohara et al. (WO2013022083, published Feb. 14, 2013).*

(Continued)

*Primary Examiner* — Chang-Yu Wang
(74) *Attorney, Agent, or Firm* — Oblon, McClelland, Maier & Neustadt, L.L.P.

(57) ABSTRACT

To provide a superior anti-human NGF antibody Fab fragment that maintains a high neutralizing activity, and that reduces systemic side-effects arising from systemic exposure while expressing a local drug effect, and means for treating postoperative pain by using such antibody fragment. An anti-human NGF antibody Fab fragment comprising a heavy-chain fragment consisting of the amino acid sequence shown by SEQ ID NO:5 and a light-chain consisting of the amino acid sequence shown by SEQ ID NO: 8.

15 Claims, No Drawings
Specification includes a Sequence Listing.

(56) References Cited

U.S. PATENT DOCUMENTS

| | | | |
|---|---|---|---|
| 2014/0147439 A1* | 5/2014 | Gearing | C07K 16/22 424/133.1 |
| 2014/0155582 A1 | 6/2014 | Kamohara et al. | |
| 2014/0170136 A1* | 6/2014 | Gearing | C07K 16/22 424/133.1 |
| 2014/0227287 A1 | 8/2014 | Kamohara et al. | |
| 2015/0017154 A1* | 1/2015 | Gearing | C07K 16/22 424/133.1 |
| 2015/0218265 A1 | 8/2015 | Kamohara et al. | |
| 2016/0272701 A1* | 9/2016 | Gearing | C07K 16/22 |

FOREIGN PATENT DOCUMENTS

| | | |
|---|---|---|
| JP | 2007-244601 | 9/2007 |
| JP | 2012-504106 A | 2/2012 |
| JP | 2014-500320 | 1/2014 |
| JP | 2014-150761 A | 8/2014 |
| WO | WO 2004/032852 A2 | 4/2004 |
| WO | 2004/058184 A2 | 7/2004 |
| WO | 2005/019266 A2 | 3/2005 |
| WO | 2006/077441 A1 | 7/2006 |
| WO | 2009/023540 A1 | 2/2009 |
| WO | WO 2010/106812 A1 | 9/2010 |
| WO | 2013/022083 A1 | 2/2013 |
| WO | 2013/183032 A2 | 12/2013 |
| WO | WO 2016-100263 | 12/2016 |

OTHER PUBLICATIONS

The factsheet of advantages of Ab fragmentation retrieved from the Thermo Fisher website: www.thermofisher.com/US/en/home/life-science/antibodies/antibodies-learning-center/antibodies-resource-library/antibody-methods/antibody-fragmentation.html on Oct. 16, 2018.*
Nelson et al. Nat. Biotechnol. 2009; 27:331-337.*
Covaceuszach et al. Pios One 2012; 7:e32212. doi:10.1371/journal.pone.0032212.*
Covaceuszach et al. Acta Cryst. 2001; D57: 1307-1309.*
Covaceuszach et al. J. Mol. Biol. 2008; 381:881-896.*
Callegaro et al. J. Mol. Recog. 1990; 3:187-191.*
Lobo et al. J. Pharma. Sci. 2004; 93:2645-2668.*
Humphreys, et al., Protein Eng. Design & Selection, 2007; 20:227-234.*
La Porte et al. mAbs;2014; 6:1059-1068.*
Covaceuszach et al. Proteins: Structure, Function and Bioinformatics, 2005; 58:717-727.*
Covaceuszach et al. Acta Cryst. 2004; D60: 1323-1327.*
Rispens et al. Chapter9, p. 159-177, Antibody Fc, 2014, Elsevier, Inc.*
Hefti, Franz F., et al., "Novel class of pain drugs based on antagonism of NGF", Trends in Pharmacological Sciences, 2006, vol. 27, pp. 85-91.
Lane, Nancy E., et al. "Tanezumab for the Treatment of Pain from Osteoarthritis of the Knee", The New England Journal of Medicine, 2010, vol. 363, pp. 1521-1531.
Evans, R. J., et al. "Proof of Concept Trial of Tanezumab for the Treatment of Symptoms Associated With Interstitial Cystitis", The Journal of Urology, 2011, vol. 185, pp. 1716-1721.
Katz, Nathaniel, et al., "Efficacy and safety of tanezumab in the treatment of chronic low back pain", Pain®, 2011, vol. 152, pp. 2248-2258.
Sanga, Panna, et al. "Efficacy, safety, and tolerability of fulranumab, an anti-nerve growth factor antibody, in the treatment of patients with moderate to severe osteoarthritis pain", Pain®, 2013, vol. 154, pp. 1910-1919.
Tiseo, Paul J., et al., "Fasinumab (REGN475), an antibody against nerve growth factor for the treatment of pain: Results from a double-blind, placebo-controlled exploratory study in osteoarthritis of the knee", Pain°, 2014, vol. 155, pp. 1245-1252.
Riviere, Gilles, et al. "Effect of Antivenom on Venom Pharmacokinetics in Experimentally Envenomed Rabbits: Toward an Optimization of Antivenom Therapy", The Journal of Pharmacology and Experimental Therapeutics, 1997, vol. 281, pp. 1-8.
Covel, David G., et al., "Pharmacokinetics of Monoclonal Immunoglobulin $G_1$, $F(ab')_2$, and Fab' in Mice", Cancer Research, Aug. 1986, vol. 46, pp. 3969-3978.
Yano, Shinya, et al., "Natural antibodies against the immunoglobulin $F(ab')_2$ fragment cause elimination of antigens recognized by the $F(ab')_2$ from the circulation", European Journal of Immunology, 1995, vol. 25, pp. 3128-3133.
International Search Report dated Aug. 16, 2016 in PCT/JP2016/065099, filed on May 20, 2016.
Extended European Search Report dated Nov. 21, 2018 in Patent Application No. 16799968.9, 8 pages.
Callegaro, L. et al. "Purification and Characterization of Fab Fragments from Anti-mouse NGF Polyclonal Antibodies" Journal of Molecular Recognition, vol. 3, No. 5-6, XP008079710, 1990, pp. 187-191.
Indonesian Office Action dated Jan. 16, 2020 in Indonesian Patent Application No. P00201709312 (with English translation), 4 pages.
Liu, H., et al., "Heterogeneity of Monoclonal Antibodies", Journal of Pharmaceutical Sciences, 2008, vol. 97, No. 7, pp. 2426-2447.
Humphreys, D.P., et al., "Formation of Dimeric Fabs Escherichia coli: effect of hinge size and isotype, presence of interchain disulphide bond, Fab' expression levels, tail piece sequences and growth conditions", Journal of Immunological Methods, 1997, vol. 209, No. 2, pp. 193-202.
Saygili, E., et al., Journal of Molecular and Cellular Cardialooy, 2010, vol. 49, p. 79-87, ISSN 0022-2828.
Gong, Y., et al., Chinese Medical Journal, 2009, vol. 122, No. 1, p. 74-82, ISSN 2542-5641.
International Search Report dated Jun. 25, 2019 in PCT/JP 2019/019045 filed May 14, 2019.
Extended European Search Report dated Dec. 10, 2021, in corresponding European patent application No. 19804443.0.
Cagnoni et al, "Central Sympathedc Inhibition: a Neglected Approach for Treatment of Cardiac Arrhythmias?", Current Hypertension Reports, 2018, pp. 1-11.
Cao et al., "Nerve Sprouting and Sudden Cardiac Death", Circulation Research, 2000, vol. 86, No. 7, pp. 818-821.

* cited by examiner

ANTI-HUMAN NGF ANTIBODY FAB FRAGMENT AND METHODS FOR TREATING POSTOPERATIVE PAIN RELATED TO NGF

CROSS REFERENCE TO RELATED APPLICATIONS

This application is a 371 of International Patent Application No. PCT/JP2016/065099, filed on May 20, 2016, and claims priority to Japanese Patent Application No. 2015-104806, filed on May 22, 2015.

BACKGROUND OF THE INVENTION

Field of the Invention

The present invention relates to a novel anti-human NGF antibody Fab fragment. The present invention also relates to a polynucleotide that comprises a base sequence encoding the anti-human NGF antibody Fab fragment, an expression vector comprising the polynucleotide, and a host cell transformed by the expression vector, and a method for producing the anti-human NGF antibody Fab fragment. The present invention further relates to a pharmaceutical composition comprising the anti-human NGF antibody Fab fragment, and a method for treating postoperative pain using the anti-human NGF antibody Fab fragment.

Discussion of the Background

A nerve growth factor (NGF) is one of humoral factors generally called "neurotrophic factors", and plays an important role in generation and differentiation of neurons and in maintaining functions of neurons in the body. As NGF receptors, a high affinity trkA (tropomyosin receptor kinase A) and a low affinity p75NTR (p75 neurotrophin receptor) are known. Among these, there is a report reporting that the p75NTR binds to all of the neurotrophic factors and is involved in apoptosis in the process of neuronal generation. However, the role of the p75NTR has not yet been sufficiently explained. Meanwhile, it is known that knockout mice of the NGF and the trkA express the same phenotype (NPL1), and it is considered that the physiological action of NGF is expressed mainly via the trkA.

It has been reported that an administration of NGF induces pain in rats (NPL 2), and that an intravenous administration of NGF to human induces muscular pain in whole body, and a local application of NGF induces hyperalgesia and allodynia at the site of NGF administration as well as whole body pain (NPL 3). The amount of NGF expressed in animals is known to increase when tissues are injured by incision of the muscle tissue (NPL 4) and the skin tissue (NPL 5) in animals such as rat models of postoperative pain. With regards to the pathological condition of human pain, it has been verified that the expression of NGF and trkA are accelerated in an articular cartilage with osteoarthritis (OA) (NPL6), that the NGF level is increased in exudates from the incised section when a caesarean operation is performed (NPL 7), and that the NGF level of patients with rheumatoid arthritis (NPL 8) or interstitial cystitis (NPL 9) is increased.

To date, it has been reported that pain is suppressed in various animal pain models when the NGF signal is inhibited (NPL 10, PTLs 1 to 3).

Anti-human NGF antibodies have been reported thus far, REGN475 (PTL 2), 1-15(N52D-A)-Fab'-PEG (PTL 3), Fulranumab (PTL 4), and MEDI-578 (PTL 5) as fully human anti-human NGF antibodies, and Tanezumab (PTL 6) and PG110 (PTL 7) as humanized anti-human NGF antibodies. Among these, the subcutaneous administration of Tanezumab in addition to its intravenous administration is reported to exhibit an extensive analgesic effect on pain such as arthralgia accompanying osteoarthritis, chronic back pain, and cystalgia accompanying interstitial cystitis (NPLs 11 to 13) in clinical settings.

Many medicines have been reported to show side effects, and anti-NGF antibodies are no exception. There has been reports of harmful events arising from administration of the anti-NGF antibody to human, such as headaches, upper respiratory tract infection, and paresthesia in relation to the clinical study of tanezumab (NPL 11); perception disorder, headaches, and rhinopharyngitis in relation to the clinical study of fulranumab (NPL 14); and arthralgia, hyperesthesia, muscle ache, peripheral edema, and arthrocele in relation to the clinical study of REGN475 (NPL 15).

Generally speaking, when a medicine is exposed to tissues other than the target tissue, it causes undesirable side effects for the human body in the tissues.

Commonly developed are pharmaceutical agents for local administration that prevent or reduce side effects by raising the tissue concentration at the administered site and by reducing exposure of other tissues via systemic blood circulation through direct administration to the target tissue.

There are many therapeutic antibodies that can be administered subcutaneously or intramuscularly in addition to ones administered by intravascular administration into veins, etc. After the subcutaneous or intramuscular administration, antibodies are immediately transferred into blood through the lymphatic and then circulated throughout the body. Many therapeutic antibodies, after being transferred into blood, are circulated in the blood flow to be delivered to the target tissue where they exhibit pharmacological effects. Further, many therapeutic antibodies show a predominant distribution in blood, and a low penetration into target tissue (tissue/blood concentration ratio). Hence, high concentration of many therapeutic antibodies in blood must be essential to keep the effective concentration at the target tissue (NPL 16). Furthermore, many therapeutic antibodies have half-life in blood ranging from several days to a month, and keep the long lasting sustainable concentration in blood to retain the pharmacological effect for a prolonged period. As such, even if a common therapeutic antibody is administered to a local site such as subcutaneous or intramuscular site, it will still produce a systemic pharmacological effect/side-effect by remaining in blood to be circulated to the whole body.

Multimerization including dimerization becomes a serious problem when trying to guarantee stable and uniform quality in the field of biologics, such as therapeutic antibodies.

$F(ab')_2$, which is a dimer of Fab', is known to have a different pharmacokinetics from Fab' (NPLs 17 and 18).

It has been reported that the natural antibody against $F(ab')_2$, which is a dimer of Fab', causes antibody elimination (NPL 19). This kind of antigen-antibody reaction affects the pharmacokinetics of the pharmaceutical agent so that the antibody is eliminated more quickly, and also poses risks of anaphylaxis reaction, etc. As seen, there are several risks associated with $F(ab')_2$.

CITATION LIST

Patent Literatures

PTL 1: WO 2013/183032
PTL 2: WO 2009/023540

PTL 3: WO 2013/022083
PTL 4: WO 2005/019266
PTL 5: WO 2006/077441
PTL 6: WO 2004/058184
PTL 7: U.S. Pat. No. 8,435,523

Non-Patent Literatures

NPL 1: "Reviews in the Neurosciences", 1997, Vol. 8, p. 13-27
NPL 2: "The Journal of Neuroscience", 1993, Vol. 13, p. 2136-2148
NPL 3: "Annals of Neurology", 1994, Vol. 36, p. 244-246
NPL 4: "Anesthesiology", 2009, Vol. 110, p. 140-149
NPL 5: "Pain", 2005, Vol. 117, p. 68-76
NPL 6: "Rheumatology", 2002, Vol. 41, p. 1413-1418
NPL 7: "The Journal of Pain", 2008, Vol. 9, p. 650-657
NPL 8: "Clinical and Experimental Rheumatology", 1997, Vol. 15, p. 433-438
NPL 9: "British Journal of Urology", 1997, Vol. 79, p. 572-577
NPL 10: "Trends in Pharmacological Sciences", 2006, Vol. 27, p. 85-91
NPL 11: "The New England Journal of Medicine", 2010, Vol. 363, p. 1521-1531
NPL 12: "The Journal of Urology", 2011, Vol. 185, p. 1716-1721
NPL 13: "Pain", 2011, Vol. 152, p. 2248-2258
NPL 14: "Pain", 2013, Vol. 154, p. 1910-1919
NPL 15: "Pain", 2014, Vol. 155, p. 1245-1252
NPL 16: "Bioanalysis", 2013, Vol. 5, p. 2003-2014
NPL 17: "The Journal of Pharmacology and Experimental Therapeutics", 1997, Vol. 281, p. 1-8
NPL 18: "Cancer Research", 1986, Vol. 46, p. 3969-3978
NPL 19: "European Journal of Immunology", 1995, Vol. 25, p. 3128-3133

SUMMARY OF INVENTION

Technical Problem

The object of the present invention is to provide a superior anti-human NGF antibody Fab fragment that maintains a high neutralizing activity, and that reduces systemic side-effects arising from systemic exposure, while expressing a local pharmacological effect.

Solution to Problem

The present invention includes the following inventions of products and methods that have medical and industrial usefulness.

In other words, an embodiment of the present invention may be in the following form.

(1) An anti-human NGF antibody Fab fragment selected from a group consisting of (a) and (b) below:
(a) an anti-human NGF antibody Fab fragment comprising a heavy-chain fragment consisting of the amino acid sequence shown by SEQ ID NO: 5 and a light-chain consisting of the amino acid sequence shown by SEQ ID NO: 8; and,
(b) an anti-human NGF antibody Fab fragment derived from posttranslational modification of the anti-human NGF antibody Fab fragment of (a).

(2) The anti-human NGF antibody Fab fragment according to (1), comprising a heavy-chain fragment consisting of the amino acid sequence shown by SEQ ID NO: 5 and a light-chain fragment consisting of the amino acid sequence shown by SEQ ID NO: 8.

(3) The anti-human NGF antibody Fab fragment according to (1), wherein said posttranslational modification is pyroglutamylation at N-terminus of a heavy-chain variable region.

(4) The anti-human NGF antibody Fab fragment according to (1), comprising a heavy-chain fragment consisting of the amino acid sequence shown by SEQ ID NO: 5, where a glutamine at amino acid position 1 of SEQ ID NO: 5 is modified to a pyroglutamic acid, and a light-chain fragment consisting of the amino acid sequence shown by SEQ ID NO: 8.

(5) A polynucleotide comprising a base sequence encoding the heavy-chain fragment of the anti-human NGF antibody Fab fragment according to (1).

(6) An expression vector selected from a group consisting of (a) and (b) shown below:
(a) an expression vector comprising a polynucleotide comprising a base sequence encoding the heavy-chain fragment of the anti-human NGF antibody Fab fragment according to (1), and a polynucleotide comprising a base sequence encoding the light-chain of said anti-human NGF antibody Fab fragment; and
(b) an expression vector comprising a polynucleotide comprising a base sequence encoding the heavy-chain fragment of the anti-human NGF antibody Fab fragment according to (1).

(7) A host cell transformed with the expression vector according to (6).

(8) The host cell according to (7) selected from a group consisting of (a) and (b) shown below:
(a) a host cell transformed with an expression vector comprising a polynucleotide comprising a base sequence encoding the heavy-chain fragment of the anti-human NGF antibody Fab fragment according to (1), and a polynucleotide comprising a base sequence encoding the light-chain of said anti-human NGF antibody Fab fragment; and
(b) a host cell transformed with an expression vector comprising a polynucleotide comprising a base sequence encoding the heavy-chain fragment of the anti-human NGF antibody Fab fragment according to (1), and with an expression vector comprising a polynucleotide comprising a base sequence encoding the light-chain of the said anti-human NGF antibody Fab fragment.

(9) A method for producing an anti-human NGF antibody Fab fragment, comprising culturing the host cell according to (8) to express an anti-human NGF antibody Fab fragment.

(10) An anti-human NGF antibody Fab fragment capable of being produced by the method according to (9).

(11) A pharmaceutical composition comprising the anti-human NGF antibody Fab fragment according to any one of (1)-(4) and (10) and a pharmaceutically acceptable carrier.

(12) The pharmaceutical composition according to (11), which is a local pharmaceutical composition for treating postoperative pain.

(13) A pharmaceutical composition comprising the anti-human NGF antibody Fab fragment according to (2), the anti-human NGF antibody Fab fragment according to (4), and a pharmaceutically acceptable carrier.

(14) The pharmaceutical composition according to (13), which is a local pharmaceutical composition for treating postoperative pain.

(15) A use of the anti-human NGF antibody Fab fragment according to any one of (1)-(4) and (10), in the manufacture of a local pharmaceutical composition for treating postoperative pain.
(16) A use of the anti-human NGF antibody Fab fragment according to any one of (1)-(4) and (10), for a treatment of postoperative pain by local administration.
(17) The anti-human NGF antibody Fab fragment according to any one of (1)-(4) and (10) for use in local administration to treat postoperative pain.
(18) A method for treating postoperative pain comprising locally administering an effective amount of the anti-human NGF antibody Fab fragment according to any one of (1)-(4) and (10) to a subject.

Advantageous Effect of Invention

The anti-human NGF antibody Fab fragment of the present invention is effective in the treatment of postoperative pain whose pathological condition develops under the influence of human NGF. The thus characterized anti-human NGF antibody Fab fragment of the present invention is marked by superior pharmacokinetics, such as high neutralization activity and local retention as well as swift elimination from blood, so that it reduces dosage and prolongs drug effect as well as reduce systemic side-effects from systemic exposure and thereby is expected to provide a remarkable improvement in both the effect and safety of the drug for clinical application. The anti-human NGF antibody Fab fragment of the present invention contributes greatly to the treatment of postoperative pain which is related to human NGF.

DETAILED DESCRIPTION OF THE PREFERRED EMBODIMENTS

The present invention is described in detail below, but these descriptions do not limit the scope of the invention. Unless otherwise defined herein, scientific terms and technical terms used in relation to the present invention hold the meaning generally understood by a person skilled in the art.

The present inventors performed extensive studies on how to prepare anti-human NGF antibodies or antigen binding fragments thereof, and succeeded in obtaining a superior anti-human NGF antibody Fab fragment that retains a high neutralization activity as well as expresses effect of the drug locally while reducing the systemic side-effect arising from systemic exposure.

The basic structure of an antibody molecule is common among the respective antibody classes and is constituted with heavy-chains having a molecular weight of 50,000 to 70,000 and light-chains having a molecular weight of 20,000 to 30,000. The heavy-chain generally consists of a polypeptide chain including about 440 amino acids, and each class has its characteristic structure. The heavy-chains are called γ, μ, α, δ, and ε chains corresponding to IgG, IgM, IgA, IgD, and IgE. Furthermore, IgG has subclasses such as IgG1, IgG2, IgG3, and IgG4, and these chains are called γ1, γ2, γ3, and γ4 respectively. The light-chain generally consists of a polypeptide chain including about 220 amino acids, and two types of the light-chain including an L-type and a K-type light-chains are known, which are called λ and κ chains respectively. Regarding the peptide constitution of the basic structure of an antibody molecule, two homologous heavy-chains and two homologous light-chains are bound via disulfide bonds (S—S bonds) and non-covalent bonds, and the molecular weight thereof is 150,000 to 190,000. The two kinds of light-chains can be paired with any heavy-chain. Each antibody molecule always consists of two identical light-chains and two identical heavy-chains.

There are four intrachain S—S bonds in a heavy-chain (five bonds for μ and ε chains) and two in a light-chain. One loop is formed per 100 to 110 amino acid residues, and this steric structure is similar among the respective loops and is called a structural unit or a domain. For both heavy-chains and light-chains, the amino acid sequence of the domain positioned at the N-terminal thereof is not constant, even in a reference standard from the same class (subclass) of the same animal species, and this domain is called a variable region. Each of the domains is called a heavy-chain variable region (VH) and a light-chain variable region (VL) respectively. Since the amino acid sequence of the C-terminal side from the variable region is almost constant in each class or subclass, this region is called a constant region, and each of the domains are described as CH1, CH2, CH3 and CL, respectively.

The antigenic determinant site of an antibody is constituted with VH and VL, and the binding specificity depends on the amino acid sequence of this site. On the other hand, biological activities such as binding to complements or various cells reflect the differences in the constant region structure among the various classes of Ig. It is known that the variability in the variable regions of the heavy-chain and light-chain is mostly limited to three small hypervariable regions present in both chains, and these regions are called complementarity determining regions (CDRs; CDR1, CDR2 and CDR3 starting from the N-terminal side). The remaining portion of the variable region is called a framework region (FR) and is relatively constant.

A region between the CH1 domain and the CH2 domain of the heavy-chain constant region of an antibody is called a hinge region. This region includes lots of proline residues and has a plurality of inter-chain S—S bonds connecting two heavy-chains. For example, each hinge region of human IgG1, IgG2, IgG3, and IgG4 includes 2, 4, 11, and 2 cysteine residues respectively which constitute the inter-heavy-chain S—S bonds. The hinge region is a region highly sensitive to a proteolytic enzyme such as papain or pepsin. When an antibody is digested with papain, its heavy chain is cleaved at a position closer to the N-terminal side than to the inter-heavy-chain S—S bond of the hinge region, whereby the antibody is broken down into two Fab fragments and one Fc fragment. The Fab fragment is constituted with a light-chain and a heavy-chain fragment including a heavy-chain variable region (VH), a CH1 domain, and a portion of the hinge region. When an antibody is digested with pepsin, its heavy-chain is cleaved at a position closer to the C-terminal side than to the inter-heavy-chain S—S bond of the hinge region, whereby F(ab')$_2$ fragments is generated. The F(ab')$_2$ fragment is a fragment having a dimeric structure in which two Fab' fragments bind to each other via the inter-heavy-chain S—S bond in the hinge region. The Fab' fragment is constituted with a light-chain and a heavy-chain fragment including a heavy-chain variable region (VH), a CH1 domain, and a portion of the hinge region. Cysteine residues constituting the inter-heavy-chain S—S bond are included in the portion of the hinge region. All of the Fab fragment, F(ab')$_2$ fragment, and Fab' fragment include the variable region and have antigen-binding activity.

The anti-human NGF antibody Fab fragment of the present invention obtained successfully by the present inventors is a Fab fragment with the following features:

An anti-human NGF antibody Fab fragment comprising a heavy-chain fragment consisting of the amino acid sequence shown by SEQ ID NO: 5 and a light-chain consisting of the amino acid sequence shown by SEQ ID NO: 8.

Specifically, the present inventors modified a fully human anti-human NGF antibody 1-15 (N52D-A)-Fab' fragment (PTL 3; it is also called as "1-15 (N52D-A)-Fab'" in said document), and by screening antibodies using various biological activity tests and physical property tests, they succeeded in identifying the anti-human NGF antibody Fab fragment of the present invention as an anti-human NGF antibody Fab fragment that is stable and retains high neutralizing activity and local accumulation.

The anti-human NGF antibody Fab fragment of the present invention may be readily prepared by a person skilled in the art based on the sequence information disclosed in the present specification using a commonly known method. For example, the anti-human NGF antibody Fab fragment of the present invention may be produced by synthesizing a polynucleotide comprising a base sequence encoding its heavy-chain fragment and a polynucleotide comprising a base sequence encoding its light chain, and connecting the same to suitable expression vectors. Subsequently, the expression vectors are introduced into culture cells. Finally, when the cells are cultured, the person skilled in the art can obtain monoclonal Fab fragments from the culture supernatant.

The polynucleotide comprising the base sequence encoding the heavy-chain fragment of the Fab fragment of the present invention and the polynucleotide comprising the base sequence encoding the light-chain of the Fab fragment of the present invention may be synthesized, for example, based on the base sequence designed according to the amino acid sequences of the heavy-chain fragment and the light-chain by using gene synthesis methods commonly known in the field of art. For example, the synthesis method of an antibody gene set forth in WO 90/07861 and other methods commonly known to a person skilled in the art may be used as such gene synthesis methods.

In one embodiment, as a polynucleotide comprising a base sequence encoding the heavy-chain fragment of the anti-human NGF antibody Fab fragment consisting of the amino acid sequence shown by SEQ ID NO: 5, a polynucleotide comprising a base sequence shown by SEQ ID NO: 1 may be listed as an example. As a polynucleotide comprising a base sequence encoding the light-chain of the anti-human NGF antibody Fab fragment consisting of the amino acid sequence shown by SEQ ID NO: 8, a polynucleotide comprising a base sequence shown by SEQ ID NO: 4 may be listed as an example.

Processes following the preparation of the polynucleotide comprising the base sequence encoding the heavy-chain fragment of the Fab fragment of the present invention and the polynucleotide comprising the base sequence encoding the light-chain of the Fab fragment of the present invention, such as the introduction of the polynucleotide to an expression vector, the introduction of an expression vector to a culture cell, the incubation of the culture cell, and the purification of the Fab fragment, may be performed using various methods commonly known in the field of art.

Expression vectors that can be used include, for example, the GS vectors pEE6.4 or pEE12.4 (Lonza), but there is no particular limitation as long as the vector is capable of expressing the polynucleotide comprising the base sequence encoding the heavy-chain fragment of Fab fragment of the present invention and/or the polynucleotide comprising the base sequence encoding the light-chain of Fab fragment of the present invention, thereby capable of producing polypeptides encoded by the same.

The above expression vectors are introduced into the culture cell by methods such as calcium phosphate transfection or electroporation.

Culture cells into which the expression vectors are to be introduced may be, for example, the CHO-K1SV cells, the CHO-DG44 cells, and the 293 cells, and they may be cultured by a common method.

After the above culturing, the Fab fragments accumulated in the culture supernatant may be purified by various column chromatography methods, such as that using KappaSelect.

An example of the anti-human NGF antibody Fab fragment of the present invention includes an h1f.6 antibody described in the EXAMPLES section below.

When an antibody is expressed in cells, it is known that the antibody is subjected to posttranslational modifications. An example of the posttranslational modifications includes a cleavage of lysine at C-terminus of a heavy-chain by a carboxypeptidase, a modification of glutamine or glutamic acid at N-terminus of a heavy-chain or a light-chain to pyroglutamic acid by pyroglutamylation, glycosylation, oxidation, deamidation, glycation, and the like. It is known in the art that such posttranslational modifications occur to various antibodies (J. Pharm. Sci., 2008, Vol. 97, p. 2426-2447).

The anti-human NGF antibody Fab fragment of the present invention may include an anti-human NGF antibody Fab fragment which is subjected to the posttranslational modification(s). An example of the anti-human NGF antibody Fab fragment which may be subjected to posttranslational modification(s) include, an anti-human NGF antibody Fab fragment of which N-terminus of the heavy-chain variable region is pyroglutamylated. Such posttranslational modification through pyroglutamylation at N-terminus is known in the art as not affecting the activity of an antibody (Anal. Biochem., 2006, Vol. 348, p. 24-39).

For example, the anti-human NGF antibody Fab fragment of the present invention includes following anti-human NGF antibody Fab fragment:

An anti-human NGF antibody Fab fragment comprising a heavy-chain fragment consisting of the amino acid sequence shown by SEQ ID NO: 5, where a glutamine at amino acid position 1 of SEQ ID NO:5 is modified to a pyroglutamic acid, and a light-chain consisting of the amino acid sequence shown by SEQ ID NO: 8.

The anti-human NGF antibody Fab fragment of the present invention binds to human NGF. The binding activity of the obtained anti-human NGF antibody Fab fragment to human NGF may be measured by ELISA, FACS, etc. For example, if ELISA is to be used, human NGF is immobilized to ELISA plate and the Fab fragment is added to this ELISA plate, after which a secondary antibody such as an anti-kappa antibody labeled with biotin, etc. and a streptavidin labeled with alkaline phosphatase are added. Then, activity is measured using a reagent for detecting activity (e.g. a chemiluminescent alkaline phosphatase substrate for alkaline phosphatase labels) to identify the bonding of the secondary antibody. In addition, the anti-human NGF antibody Fab fragment of the present invention may bind with other animal-derived NGF (e.g. mouse NGF) in addition to the human NGF, and the binding activity with these proteins may be measured as well.

The anti-human NGF antibody Fab fragment of the present invention has a neutralizing activity against human NGF. As used in the present specification, the term "neutralizing activity" of an anti-human NGF antibody Fab fragment refers to an activity to inhibit any biological activity induced through human NGF by binding to human NGF, and it may be evaluated using a single or multiple biological activities of human NGF as the indicator. Such neutralizing activity includes, for example, a binding inhibition activity between human NGF and its receptor human trkA, and it may be evaluated using methods described in the EXAMPLES section below.

In order to evaluate the effect of the anti-human NGF antibody Fab fragment of the present invention in more detail, it is also possible to perform an in vivo study. For example, it is possible to perform as shown in the EXAMPLES section below, a study of analgesic effects using a rat postoperative pain model after plantar incision, to evaluate the in vivo drug effect of the anti-human NGF antibody Fab fragment. It is also possible to confirm pharmacological activity of an anti-human NGF antibody Fab fragment in a tissue by conducting a study evaluating a binding activity for NGF or a study evaluating a binding inhibition activity between NGF and its receptor trkA, by using a tissue homogenate obtained after local administration of an anti-human NGF antibody Fab fragment to femoral muscle in rats. Further, it is also possible to perform a study for evaluating the concentration of Fab fragment in plasma or tissues to evaluate the retention of local exposure level of Fab fragment as well as the reduction of the systemic exposure in blood.

As other method, methods for evaluating the stability of the anti-human NGF antibody Fab fragment of the present invention (e.g. thermostability, prolonged storage stability, and high concentration stability) include a method that measures aggregation during storage by size exclusion chromatography.

The anti-human NGF antibody Fab fragment of the present invention may be formulated by a common method after purification, performed as necessary, to be used for the treatment of postoperative pain.

The term "postoperative pain" refers to pain that is caused by or that occurs as a result of traumatic injuries such as a cut wound, stabbing, incision, laceration or injuries in the tissue of an individual (include those caused by all surgical treatments whether it be invasive or noninvasive). The term postoperative pain used in the present specification does not include pain occurring without any physical injury from external causes (i.e., pain which is not caused by injury or which is not resulting from injury). A postoperative pain is an internal or external (including peripheral) pain, and a wound, a cut wound, an injury, a laceration or an incision may be inflicted accidentally (in case of external injury/wound) or intentionally (in case of incision in an operation). The pain may be evaluated objectively or subjectively using a pain score and other methods well known in the field of art. Postoperative pain as used in the present specification includes allodynia (i.e. usually, an increase in the amount of response to a non-noxious stimulus) and hyperpathia (i.e. usually, an increase in the amount of response to a noxious or unpleasant stimulus), and these may be of a thermal or mechanical nature. Pains are characterized by thermosensitivity, sensitivity against mechanical stimulus and/or pain at rest. Postoperative pain includes pain induced against mechanical stimulus and pain at rest.

The anti-human NGF antibody Fab fragment of the present invention may be used as a therapeutic agent for postoperative pain. Examples of the formulation of a therapeutic agent include parenteral agents such as injections, drops and depots, and administration by intramuscular injection or hypodermal injections to the local target tissue is preferred. It is also possible when forming a pharmaceutical formulation to use carriers and additives that suit the formulation as long as they are pharmaceutically acceptable.

The amount of the anti-human NGF antibody Fab fragment of the present invention to be added when forming the above pharmaceutical formulation differs by the level of the symptom and age of the patient, the shape of the pharmaceutical formulation to be used, or the valence of the antibody, but an amount of about 0.001 mg/kg to 100 mg/kg may be used.

The present invention also relates to a pharmaceutical composition comprising the anti-human NGF antibody Fab fragment of the present invention. The pharmaceutical composition of the present invention may comprise pharmaceutically acceptable carriers or additives. Such pharmaceutically acceptable carriers or additives are not particularly limited, and carriers or additives well known to a person skilled in the art may be used. The present invention also relates to the anti-human NGF antibody Fab fragment of the present invention for use in the treatment of postoperative pain and the use of the anti-human NGF antibody Fab fragment of the present invention in the manufacture of a pharmaceutical composition for treating postoperative pain. The present invention also relates to a method for treating postoperative pain comprising locally administering an effective amount of the anti-human NGF antibody Fab fragment of the present invention to a subject. Note that a "subject" is a human or other mammalians requiring the treatment, and one embodiment is a human in need of the treatment. The effective amount of the anti-human NGF antibody Fab fragment in the treatment method of the present invention may be an amount similar to the amount of Fab fragment added when forming a pharmaceutical formulation as mentioned above. In addition, the local pharmaceutical composition of the present invention refers to a pharmaceutical composition administered or used on a site requiring treatment, or sites neighboring that site, particularly the target tissue such as the tissue dissected in a surgical operation or the surrounding area. For example, the pharmaceutical composition may be administered by intramuscular injection or hypodermal injections to the local target tissue as mentioned above. The present invention includes a case of the anti-human NGF antibody Fab fragment of the present invention being retained at the local target tissue for a certain time, preferably 72 h., and more preferably 24 h.

The pharmaceutical composition of the present invention may comprise plural kinds of the anti-human NGF antibody Fab fragment for the present invention. For example, the present invention also includes a pharmaceutical composition comprising an anti-human NGF antibody Fab fragment which is not subjected to the posttranslational modification and an anti-human NGF antibody Fab fragment derived from the posttranslational modification.

In one embodiment, the pharmaceutical composition of the present invention includes a pharmaceutical composition comprising anti-human NGF antibody Fab fragments as shown in (a) and (b) below:

(a) an anti-human NGF antibody Fab fragment comprising a heavy-chain fragment consisting of the amino acid sequence shown by SEQ ID NO: 5 and a light-chain consisting of the amino acid sequence shown by SEQ ID NO: 8; and (b) an anti-human NGF antibody Fab fragment derived from posttranslational modification of the anti-human NGF antibody Fab fragment of (a).

In one embodiment, the pharmaceutical composition of the present invention includes a pharmaceutical composition comprising anti-human NGF antibody Fab fragments as shown in (a) and (b) below:

(a) an anti-human NGF antibody Fab fragment comprising a heavy-chain fragment consisting of the amino acid sequence shown by SEQ ID NO: 5 and a light-chain consisting of the amino acid sequence shown by SEQ ID NO: 8; and
(b) an anti-human NGF antibody Fab fragment comprising a heavy-chain fragment consisting of the amino acid sequence shown by SEQ ID NO:5, where a glutamine at amino acid position 1 of SEQ ID NO:5 is modified to a pyroglutamic acid, and a light-chain fragment consisting of the amino acid sequence shown by SEQ ID NO:8.

The present invention also relates to a polynucleotide comprising a base sequence encoding a heavy-chain fragment of the anti-human NGF antibody Fab fragment of the present invention, and a polynucleotide comprising a base sequence encoding a light-chain of the anti-human NGF antibody Fab fragment of the present invention (which may hereinafter collectively referred to as "the polynucleotide of the present invention"), and an expression vector comprising one or both of such polynucleotides (which may hereinafter referred to as "the expression vector of the present invention").

The expression vector of the present invention is not limited to a particular type as long as it expresses a polynucleotide comprising the base sequence encoding the heavy-chain fragment of the anti-human NGF antibody Fab fragment of the present invention and/or a polynucleotide comprising the base sequence encoding the light chain of the anti-human NGF antibody Fab fragment of the present invention in various host cells that are prokaryotic cells and/or eukaryotic cells and is capable of producing a polypeptide(s) encoded by said nucleotide(s). Examples of expression vectors to be used include a plasmid vector, a virus vector (e.g. adenovirus, retrovirus), for example, GS vector pEE6.4 and pEE12.4 (Lonza) may be used. In one embodiment, the expression vector of the present invention is an expression vector which comprises a polynucleotide comprising a base sequence encoding the heavy-chain fragment of the anti-human NGF antibody Fab fragment of the present invention. In another embodiment, the expression vector of the present invention is an expression vector which comprises a polynucleotide comprising a base sequence encoding the heavy-chain fragment of the anti-human NGF antibody Fab fragment of the present invention and a polynucleotide comprising a base sequence encoding the light-chain of such anti-human NGF antibody Fab fragment.

The expression vector of the present invention may comprise a promoter operably linked to the polynucleotide of the present invention. Promoters that enable expression of a gene encoding the Fab fragment of the present invention or the heavy-chain variable region and/or light-chain variable region of the same in a bacterium include the Trp promoter, lac promoter, recA promoter, λPL promoter, lpp promoter, and tac promoter when the host is a bacterium of the genus Escherichia. Promoters that enable expression in yeast include, for example, the PH05 promoter, PGK promoter, GAP promoter, and ADH promoter, and promoters that allow expression in a bacterium of the genus Bacillus include the SL01 promoter, SP02 promoter, and penP promoter. Promoters for a host cell that is an eukaryotic cell like cells of mammals include a promoter derived from SV40, a retrovirus promoter or a heat shock promoter.

When a bacterium, particularly E. coli, is used as the host cell, the expression vector of the present invention can further comprise an initiation codon, a stop codon, a terminator region and a replicable unit. When yeast, an animal cell or insect cell is used as the host, the expression vector of the present invention can include an initiation codon and a stop codon. In this case, it may include an enhancer sequence, untranslated regions on the 5' side and 3' side of a gene that encodes the anti-human NGF antibody Fab fragment of the present invention, a secretion signal sequence, a splice junction, a polyadenylation region, a replicable unit or the like. Also, it may include a selection marker that is in common use (e.g. tetracycline-resistant gene, ampicillin-resistant gene, kanamycin-resistant gene, neomycin-resistant gene, dihydrofolic acid reductase gene) according to the intended use.

The present invention also relates to a host cell transformed with the expression vector of the present invention. A host cell that is used to prepare the transformant is not limited to a particular type as long as it conforms to the aforementioned expression vector and is transformable; examples of the host cell include various cells such as natural cells or artificially established cells commonly used in the technical field of the present invention (e.g. bacteria (bacteria of the genus Escherichia, bacteria of the genus Bacillus), yeasts (the genus Saccharomyces, the genus Pichia and the like), animal cells (CHO-K1SV cell, CHO-DG44 cell, 293 cell and the like) or insect cells (e.g. Sf9) and the like. The transformation per se can be performed by any known method.

The host cell of the present invention includes following (a) and (b):
(a) a host cell transformed with an expression vector comprising a polynucleotide comprising a base sequence encoding the heavy-chain fragment of the anti-human NGF antibody Fab fragment of the present invention and a polynucleotide comprising a base sequence encoding the light-chain of said anti-human NGF antibody Fab fragment; and
(b) a host cell transformed with an expression vector comprising a polynucleotide comprising a base sequence encoding the heavy-chain fragment of the anti-human NGF antibody Fab fragment of the present invention and an expression vector comprising a polynucleotide comprising a base sequence encoding the light-chain of said anti-human NGF antibody Fab fragment.

The present invention also relates to a method for producing an anti-human NGF antibody Fab fragment, comprising steps of culturing the host cell of the present invention and expressing an anti-human NGF antibody Fab fragment. Preferably, the host cell that is used in the above method include the aforementioned host cell (a) and (b) of the present invention.

In production of an anti-human NGF antibody Fab fragment of the present invention, the transformed host cell may be cultured in a nutrient medium. The nutrient medium preferably contains a carbon source and an inorganic nitrogen source or organic nitrogen source, which are required for the growth of the host cell. Examples of the carbon source include glucose, dextran, soluble starch, sucrose and the like; examples of the inorganic nitrogen source or organic nitrogen source include ammonium salts, nitrates, amino acids, corn steep liquor, peptone, casein, meat extract, soybean cake, potato extract and the like. If desired, other nutrients (e.g. inorganic salts (e.g. calcium chloride, sodium dihydrogen phosphate, magnesium chloride), vitamins, and the like), antibiotics (for example, tetracycline, neomycin, ampicillin, kanamycin and the like) may be contained.

The host cell is cultured by a commonly known method. Culture conditions, for example, temperature, pH of the medium, and culture time are suitably selected. For example, when the host is an animal cell, an MEM medium containing about 5% to 20% fetal bovine serum (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like can be used as the medium. The pH of the medium is preferably about 6 to 8, culture is normally performed at about 30° C. to 40° C. for about 15 to 72 h., and aeration or agitation may be performed as necessary. When the host is an insect cell, for example, Grace's medium comprising fetal bovine serum (Proc. Natl. Acad. Sci. USA, Vol. 82, p. 8404, 1985) and the like can be used, and the pH of the medium is preferably about 5 to 8. Culturing is normally performed at about 20° C. to 40° C. for 15 to 100 h., and aeration or agitation may be performed as necessary. When the host is a bacterium, an actinomyces, yeast, or a filamentous fungus, for example, a liquid medium comprising the above-described nutrient sources is appropriate. A medium having a pH of 5 to 8 is preferable. When the host is *E. coli*, preferred examples of the medium include LB medium, M9 medium (Miller et al., Exp. Mol. Genet, Cold Spring Harbor Laboratory, p. 431, 1972) and the like. In this case, culture can be normally performed at 14° C. to 43° C. for about 3 to 24 h., while aeration or agitation is performed as necessary. When the host is a bacterium of the genus *Bacillus*, culturing can be normally performed at 30° C. to 40° C. for about 16 to 96 h., while aeration or agitation is performed as necessary. When the host is yeast, examples of the medium include Burkholder's minimal medium (Bostian, Proc. Natl. Acad. Sci. USA, Vol. 77, p. 4505, 1980), and the pH of the medium is desirably 5 to 8. Culturing is normally performed at about 20° C. to 35° C. for about 14 to 144 h., and aeration or agitation may be performed as necessary.

The method for producing an anti-human NGF antibody Fab fragment of the present invention further comprises, in addition to the steps of culturing the host cell of the present invention and expressing an anti-human NGF antibody Fab fragment, a step of recovering, and preferably, isolating and purifying, the anti-human NGF antibody Fab fragment from said host cell. Examples of the method of isolation and purification include methods based on differences in solubility, such as salting-out and solvent precipitation; methods based on differences in molecular weight, such as dialysis, ultrafiltration, gel filtration, and sodium dodecyl sulfate (SDS)-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like.

The anti-human NGF antibody Fab fragment of the present invention also includes an anti-human NGF antibody Fab fragment which can be produced by the method for producing an anti-human NGF antibody Fab fragment of the present invention.

Although the present invention has been generally described above, specific examples are provided herein only for a better understanding of the present invention. These examples are for illustrative purposes only and do not limit the scope of the present invention.

EXAMPLES

In steps using a commercially available kit or reagent, experiments were performed according to the attached protocols unless otherwise specified.

Example 1

Preparation of Anti-Human NGF Antibody Fab Fragments

Three types of gene fragments were amplified with Phusion High-Fidelity DNA Polymerase (Finnzymes, F-530L) using an expression vector including a polypeptide encoding the heavy-chain of 1-15 (N52D)-Fab' fragment (PTL 3) as the template and primers designed as being capable of amplifying each of the three types of gene fragments from the VH region to hinge region (SEQ ID NOs: 1, 2 and 3). The amplified regions contained HindIII on the 5' side and EcoRI on the 3' side. The obtained heavy-chain gene fragments were digested with HindIII and EcoRI (both from NEB) and inserted into expression vector pEE6.4.

These expression plasmids were introduced into *E. coli* by a common method to obtain transformed clones, and Wizard Plus SV Minipreps DNA Purification System (Promega, A1460) was used to purify plasmid DNA. Meanwhile, the light-chain gene was the same base sequence (SEQ ID NO: 4) as the light-chain gene of 1-15 (N52D-A)-Fab' fragment, and the amino acid sequence encoded by the gene is SEQ ID NO:8. pEE12.4 encoding the light-chain gene fragment was used.

The GS vector (pEE6.4) encoding the heavy-chain gene fragment of the anti-human NGF antibody Fab fragment, and the GS vector (pEE12.4) encoding the light-chain gene fragment of the anti-human NGF antibody Fab fragment were cleaved with restriction enzymes NotI and PvuI (both from NEB). Then, ligation was performed using DNA Ligation Mix (Takara Bio Inc., 6023) to construct GS vectors encoding gene fragments of both heavy-chain and light-chain of the anti-human NGF antibody Fab fragments. The obtained plasmid DNAs were used as templates for sequencing reaction, and it was demonstrated that the plasmid DNAs contain the base sequences of the cloned heavy-chain from the VH region to the hinge region and the light-chain from the VL region to the CL region. The base sequences from the VH region to the hinge region of the three types of heavy-chains are shown as SEQ ID NO: 1, SEQ ID NO: 2 and SEQ ID NO: 3. In addition, the amino acid sequences encoded by these base sequences are shown as SEQ ID NO: 5, SEQ ID NO: 6 and SEQ ID NO: 7, respectively. The three types of anti-human NGF antibody Fab fragments were prepared by combining the heavy-chain of SEQ ID NO: 1 and the light-chain of SEQ ID NO: 4, the heavy-chain of SEQ ID NO: 2 and the light-chain of SEQ ID NO: 4, and the heavy-chain of SEQ ID NO: 3 and the light-chain of SEQ ID NO: 4, and they were designated as h1f.6 antibody, h1f.7 antibody, and h1f.8 antibody, respectively.

The anti-human NGF antibody Fab fragments were expressed in two methods of transient expression and constitutive expression using the GS vectors. In the transient expression, the GS vectors were transfected into CHO-K1SV cells (Lonza) cultured in the CD-CHO medium (Invitrogen) by using the MaxCyte electroporation method (MaxCyte), and then incubated for 7 days. The anti-human NGF antibody Fab fragments were purified from the culture supernatants using KappaSelect (GE Healthcare, 17-5458-02). In constitutive expression, the GS vectors cleaved by the restriction enzyme PvuI were transfected into the CHO-K1SV cells by using the electroporation method to express anti-human NGF antibody Fab fragments. The anti-human NGF antibody Fab fragments were purified from the culture supernatants by using KappaSelect and verified by size exclusion chromatography and SDS polyacrylamide electrophoresis. To confirm posttranslational modification of the purified h1f.6 antibody, mass spectrometry was performed. As a result, a peak which is considered as N-terminal pyroglutamylation was generated for most of the antibody.

Example 2

Evaluation of the Binding Inhibition Activity of Anti-Human NGF Antibody Fab Fragments Against Human NGF To evaluate the binding inhibition activity of obtained anti-human NGF antibody Fab fragments against human NGF, human NGF-trkA competitive ELISA that looks to the binding inhibition between human NGF and its receptor trkA as the indicator was performed. Human trkA (R&D Systems, 175-TK-050) diluted with phosphate buffered saline (PBS) to a concentration of 2000 ng/mL was added into the Nunc MaxiSorp white 96-well plate (Nunc, 436110) at 50 µL/well and immobilized by being incubated overnight at 4° C. The human trkA solution was removed by reverse-centrifugation and Blocker Casein in TBS (Thermo, 37532) was added at 200 µL/well. After the plate was incubated for 30 min at room temperature, Blocker Casein in TBS was removed by reverse-centrifugation. Purified antibody samples diluted in 7 to 11 steps from about 200,000 ng/mL to about 2 ng/mL with PBS containing 0.1% bovine serum albumin (BSA) were mixed with 700 ng/mL of biotinylated human NGF at equal amounts, incubated for 30 min at room temperature, and the resulting samples were added at 100 µL/well. The biotinylated human NGF used herein was prepared by biotinylating human NGF (R&D Systems, 256-GF-100/CF) with EZ-Link NHS-PEG4-Biotin (Thermo Scientific, 21329). The biotinylation of human NGF was performed by adding 1.25 µL of 5 mM NHS-PEG4-Biotin solution to the 250 µL of 0.4 mg/mL human NGF, incubating for 2 h on ice under a shaded condition, and exchanging the solution of the reaction mixture to PBS by using Amicon Ultra-0.5 mL 3K (Millipore, UFC500324) twice according to the manual. PBS containing 0.1% BSA was prepared as the control. After the incubation for 30 min at room temperature, the plate was washed three times with a washing solution (Tris-Buffered Saline (TBS) containing 0.05% Tween-20) and 100 µL of 1,000-fold diluted alkaline phosphatase-labeled streptavidin (Thermo, 21324) in 20-fold diluted Blocking One (NacalaiTesque Inc., 03953-95) in PBS was added per well. After the incubation for 30 min at room temperature, the plate was washed with the washing solution three times and 100 µL of 5-fold diluted alkaline phosphatase substrate (Chemiluminescent AP Microwell/ Membrane Substrate, Super Sensitive, 450 nm; SurModics, APU4-0100-01) in 2 mM Tris buffer (pH 9.8) containing 0.1 mM magnesium chloride was added per well. After the incubation for 30 min at room temperature, the signal value was measured with the EnVision counter (Perkin Elmer).

Tests of 1-15 (N52D-A)-Fab' fragment, h1f.6 antibody, h1f.7 antibody, and h1f.8 antibody were performed twice. To calculate the human NGF-trkA binding inhibition rate for each antibody, the measured value of PBS containing 0.1% BSA was set to 0% and the measured value of the maximum concentration of each antibody was set to 100%. The calculated human NGF-trkA binding inhibition rate was analyzed and the $IC_{50}$ value of the antibody was calculated by three or four parameter logistic curve fitting algorithm. The geometric averages of the $IC_{50}$ values of the two runs were calculated, $IC_{50}$ values for 1-15 (N52D-A)-Fab' fragment, h1f.6 antibody, h1f.7 antibody, and h1f.8 antibody to human NGF-trkA binding inhibition were 0.30 µg/mL, 0.32 µg/mL, 0.30 µg/mL, and 0.28 µg/mL, respectively, demonstrating that their human NGF-trkA inhibition activity was approximately the same.

Example 3

Evaluation of Dimer Formation of Anti-Human NGF Antibody Fab Fragments After Incubation for 14 Days at 50° C.

The solutions of 1-15 (N52D-A)-Fab' fragment, h1f.6 antibody, h1f.7 antibody, and h1f.8 antibody were exchanged to pH 5, 6 and 7 buffers (20 mM citric acid/120 mM NaCl in pH 5 or 6, PBS in pH 7), and adjusted to 10 mg/mL, then incubated for 14 days at 50° C. to evaluate the stability.

Dimer formation before and after the incubation for 14 days at 50° C. was evaluated by LC1100 (Agilent Technologies) with TSK gel Super Sw3000 (TOSOH, 2 mmID×300 mm) size exclusion chromatography. Measurement was conducted with mobile phase solution of 0.1 M disodium hydrogen phosphate and 0.2 M L(+) arginine acidic salt with pH adjusted to 6.8 with hydrogen chloride, flow rate at 0.075 mL/min at 25° C., with detection wavelength of 280 nm and a reference wavelength of 360 nm. The measurement was performed twice to obtain an arithmetic mean, and the rate of dimer increase was obtained by subtracting the rate of dimer formation before incubation from the rate of dimer formation after incubation. Consequently, the rates of dimer increase of 1-15 (N52D-A)-Fab' fragment at pH 5, 6 and 7 were 5.4%, 17.0% and 18.2%, respectively, demonstrating that significant amounts of dimers were formed under these conditions. The rates of dimer increase of h1f.6 antibody at pH 5, 6 and 7 were 0.1%, 0.3% and 0.5%, respectively, those of h1f.7 antibody at pH 5, 6 and 7 were 0.1%, 0.3% and 0.4%, respectively, and those of h1f.8 at pH 5, 6 and 7 were 0.1%, 0.5% and 0.7%, respectively. Hence, it was shown that h1f.6 antibody, h1f.7 antibody, and h1f.8 antibody had a significantly lower dimer increase rate and were more stable than 1-15 (N52D-A)-Fab' fragment.

Example 4

Evaluation of the Binding Inhibition Activity of Anti-Human NGF Antibody Fab Fragments Against Human NGF After Incubation for 14 Days at 50° C.

The change in the binding inhibition activity of 1-15 (N52D-A)-Fab' fragment, h1f.6 antibody, h1f.7 antibody, and h1f.8 antibody against human NGF after incubation for 14 days at pH 6 and 50° C. was evaluated by using the human NGF-trkA competitive ELISA described in EXAMPLE 2. The geometric averages of the $IC_{50}$ values of the two runs were calculated, the $IC_{50}$ value for 1-15 (N52D-A)-Fab' fragment, h1f.6 antibody, h1f.7 antibody, and h1f.8 antibody to human NGF-trkA binding inhibition were 0.47 µg/mL, 0.38 µg/mL, 0.56 µg/mL, and 0.47 µg/mL, respectively, after incubation for 14 days at 50° C. The increase rates of the $IC_{50}$ value for antibodies after incubation for 14 days at 50° C. relative to that before the incubation were 59%, 21%, 87% and 68%, respectively.

According to the results, the h1f.6 antibody, h1f.7 antibody, and h1f.8 antibody are anti-NGF antibody Fab fragments that have a significantly lower dimer increase rate than 1-15 (N52D-A)-Fab' fragment upon incubation for 14 days at 50° C. It was shown that h1f.6 antibody has only a small reduction in the binding inhibition activity during the incubation and retains a high stability.

Example 5

Evaluation of the Binding Activity for Anti-Human NGF Antibodies to Human NGF by ELISA ELISA assay was used to measure the antigen binding activity of h1f.6 antibody. To evaluate the binding ability of antibodies to human NGF, test was performed using a plate immobilized with human NGF. A comparative antibody Tanezumab was used as the control.

Human NGF (R&D Systems, 256-GF-100/CF) diluted with PBS to a concentration of 1,000 ng/mL was added into the Nunc MaxiSorp white 96-well plate (Nunc, 436110) at 100 µL/well and immobilized by being incubated overnight at 4° C. Human NGF solution was removed by reverse-centrifugation and Blocker Casein in TBS (Thermo, 37532) was added at 200 µL/well, and the plate was incubated for 30 min at room temperature. Blocker Casein in TBS was removed by reverse-centrifugation and purified antibody samples diluted in 11 steps from 1,000 ng/mL to 0.01 ng/mL with PBS containing 0.1% BSA was added at 100 µL/well, and the plate was incubated for 30 min at room temperature. PBS containing 0.1% BSA was prepared as the control. The plate was washed three times with a washing solution (TBS containing 0.05% Tween-20), 100 µL of 1,000-fold diluted biotinylated anti-human Kappa light-chain antibody (IBL, 17249) in 20-fold diluted Blocking One (Nacalai Tesque, Inc., 03953-95) in PBS was added per well, and the plate was incubated for 30 mM at room temperature. The plate was washed three times with the washing solution, 100 µL of 1,000-fold diluted alkaline phosphatase-labeled streptavidin (Thermo, 21324) in 20-fold diluted Blocking One in PBS was added per well, and the plate was incubated for 0.5 h at room temperature. The plate was washed three times with the washing solution and 100 µL of 5-fold diluted alkaline phosphatase substrate (Chemiluminescent AP Microwell/Membrane Substrate, Super Sensitive, 450 nm; SurModics, APU4-0100-01) in 2 mM Tris buffer (pH 9.8) containing 0.1 mM magnesium chloride was added per well. After the incubation for 30 min at room temperature, the signal value was measured with the EnVision counter (Perkin Elmer).

Duplicate tests were performed for each antibody and an arithmetic mean was obtained. To calculate the human NGF binding rate of each antibody, the measured value of PBS containing 0.1% BSA was set to 0% and the measured value of the maximum concentration of each antibody was set to 100%. The calculated human NGF binding rate was analyzed, and the $EC_{50}$ values of the antibody were calculated by three parameter logistic curve fitting algorithm. The geometric average of the $EC_{50}$ values of the two runs was taken, the $EC_{50}$ value of h1f.6 antibody was 73.0 ng/mL, while the $EC_{50}$ value of Tanezumab was 146 ng/mL.

Example 6

Evaluation of Binding Inhibition Activity of Anti-Human NGF Antibodies Against Human NGF The competitive ELISA assay used in EXAMPLE 2 for evaluating NGF-trkA binding inhibition was used to measure the binding inhibition activity of h1f.6 antibody against human NGF. A comparative antibody Tanezumab was used as the control.

The test was performed four times for h1f.6 antibody and three times for tanezumab, and the geometric averages of the calculated $IC_{50}$ values were taken. As a result, the $IC_{50}$ value for h1f.6 antibody to human NGF-trkA binding inhibition was 0.31 µg/mL, while the $IC_{50}$ value for Tanezumab to human NGF-trkA binding inhibition was 0.86 µg/mL.

Example 7

Evaluation of the Antibody for Local Retention in Tissue, Binding Activity to Human NGF, and Functional Inhibition Activity to Human NGF After the local administration of h1f.6 antibody, the antibody concentration in the administered tissue was assessed to evaluate the local retention of the antibody. The h1f.6 antibody was locally administered into the femoral muscle in normal rats at doses of 0.3 and 3 mg/kg at n=4 each, and the antibody concentrations in the femoral muscle at 6 hours after administration was measured by the electrochemiluminescence (ECL) assay. The local administration was performed by injecting the antibody into the femoral muscle at a dose volume of 0.2 mL/kg using PBS as the solvent.

Femoral muscle homogenate was prepared by adding 2.5-fold sample volume of tissue homogenate solution (10 mM Tris, 137 mM NaCl, cOmplete, Mini (Roche), pH 8.0) to the collected femoral muscle tissue. Two types of anti-1-15 antibodies, ANA-IBL-13A and biotinylated ANA-IBL-52A, which were obtained by immunizing mouse with 1-15 antibody (PTL 3) obtained by immunizing VelocImmune mouse with human NGF, were used in the ECL assay measurement. In addition, the biotinylated ANA-IBL-52A is produced by biotinylation of ANA-IBL-52A following the technical manual for the Biotin Labeling Kit-NH2 (Dojindo Laboratories, LK03).

The ECL assay method is shown below. An anti-1-15 antibody, ANA-IBL-13A, was diluted with TBS to a concentration of 1,000 ng/mL and added to Multi-array 96-well Plate (Meso Scale Discovery, L15XA-6) at 25 µL/well. The plate was incubated for 1 h at room temperature to immobilize ANA-IBL-13A. The ANA-IBL-13A solution was removed by reverse-centrifugation, the plate was washed three times with a washing solution (TBS containing 0.05% Tween-20), and added at 150 µL/well of Blocker Casein in TBS (Thermo, 37532). After the incubation for 1 h at room temperature, Blocker Casein in TBS was removed by reverse-centrifugation and the plate was washed three times, then 25 µL of 100-fold diluted femoral muscle homogenate in a diluent (Blocker Casein in TBS containing 0.05% Tween-20) and, for samples which were necessary to be diluted further, diluted with the diluent containing 1% of an antibody-free femoral muscle homogenate to fall under the range of the calibration curve, was added per well. To create a calibration curve of the femoral muscle homogenate, h1f.6 antibody diluted in 10 steps ranging from 10,000 ng/mL to 0.51 ng/mL by using the diluent was 100-fold diluted with the diluent containing 1% of an antibody-free femoral muscle homogenate. The diluent containing 1% of the antibody-free femoral muscle homogenate was prepared as the control. After the incubation for 1 h at room temperature, the solution was removed by reverse-centrifugation, the plate was washed three times with the washing solution, and 25 μL of the biotinylated ANA-IBL-52A diluted to 300 ng/mL with the diluent was added per well. After the incubation for 1 h at room temperature, the solution was removed by reverse-centrifugation, the plate was washed three times with the washing solution, and 25 μL of MSD SULFO-TAG Streptavidin (Meso Scale Discovery, R32AD-1) diluted to 1,000 ng/mL with the diluent was added per well. After the incubation for 1 h at room temperature, the solution was removed by reverse-centrifugation and the plate was washed three times with the washing solution. After 150 μL of MSD Read Buffer T(4×) with Surfactant (Meso Scale Discovery, R92TC-2) 2-fold diluted with ultra-pure water (MilliQ (registered trademark), Merck) was added per well, the electrochemiluminescence of the samples was measured using SECTOR Imager 6000 (Meso Scale Discovery).

A calibration curve was created to calculate the antibody concentration. The regression equation was analyzed by four parameter logistic curve fitting algorithm. Using the calibration curve, the antibody concentrations in the femoral muscle were calculated for each point. Each test was performed in duplicates, and the arithmetic mean of the concentrations was calculated.

After local administration of h1f.6 antibody at 0.3 and 3 mg/kg into the femoral muscle, the concentrations in the femoral muscle were 2.66 μg/mL and 67.9 μg/mL, respectively, at 6 hours after administration.

To evaluate the amount of h1f.6 antibody which has binding activity to human NGF in the femoral muscle, human NGF binding ELISA was performed.

Human NGF (R&D Systems, 256-GF/CF) diluted with PBS to a concentration of 1,000 ng/mL was added into the Nunc MaxiSorp white 384-well plate (Nunc, 460372) at 20 μL/well and immobilized by being incubated overnight at 4° C. The human NGF solution was removed by reverse-centrifugation, the plate was added at 80 μL/well of Blocking One (Nacalai Tesque, Inc., 03953-95), and the plate was incubated for 1 h at room temperature. The plate was washed three times with a washing solution (TBS containing 0.05% Tween-20), and 20 μL of femoral muscle homogenate of the 0.3 mg/kg administration group and the 3 mg/kg administration group which were diluted 10-fold and 100-fold, respectively, with 10-fold diluted Blocking One in TBS containing 0.05% Tween-20, was added per well.

To create a calibration curve for the femoral muscle homogenate of the 0.3 mg/kg administration group and the 3 mg/kg administration group, h1f.6 antibodies were diluted in 11 steps ranging from 3,000 ng/mL to 0.03 ng/mL with a diluent prepared by adding the antibody-free femoral muscle homogenate at 10% and 1%, respectively, to Blocking One which was 10-fold diluted with a TBS containing 0.05% Tween-20, and added at 20 μL/well.

After the incubation for 1 h at room temperature, the plate was washed three times with the washing solution and 20 μL of 2,500-fold diluted biotinylated anti-human Kappa light-chain antibody (IBL, 17249) in 10-fold diluted Blocking One in TBS containing 0.05% Tween-20 was added per well. After the incubation for 1 h at room temperature, the plate was washed three times with the washing solution, 20 μL of 8,000-fold diluted high sensitivity streptavidin-HRP (Thermo, 21130) in 10-fold diluted Blocking One in TBS containing 0.05% Tween-20 was added per well, and the plate was incubated for 1 h at room temperature. The plate was washed three times with the washing solution and 20 μL of chemiluminescent substance (BM Chemiluminescence ELISA Substrate (POD); Roche, 11582950001) was added per well, then the signal value was measured with the EnVision counter (Perkin Elmer). Each test was performed in duplicates, and the calibration curve was created to calculate the amount of h1f.6 antibody which has binding activity to human NGF. The regression equation was analyzed by four parameter logistic curve fitting algorithm, and the amount of antibody which has the human NGF binding activities were calculated for each point based on the calibration curve. The amount of h1f.6 antibody which has binding activities to human NGF in the femoral muscle were calculated by multiplying the obtained values of the 0.3 mg/kg administration group and the 3 mg/kg administration group by 35 and 350, respectively, and the arithmetic mean was obtained.

Consequently, the amount of the h1f.6 antibody which has binding activity to human NGF in the 0.3 mg/kg administration group was 2.12 μg/mL and that in the 3 mg/kg administration group was 77.9 μg/mL.

These results, which relate to a concentration of h1f.6 antibody and an amount of h1f.6 antibody having human NGF binding activity in the femoral muscle, showed that nearly all of the antibody existing in the femoral muscle was confirmed as the antibody which has binding activity to human NGF.

Next, to evaluate the binding inhibition activity to human NGF in the femoral muscle, human NGF-trkA competitive ELISA that looks to the binding inhibition between human NGF and its receptor trkA as the indicator was performed.

Human trkA (R&D Systems, 175-TK-050) diluted with PBS to a concentration of 2,000 ng/mL was added into the Nunc MaxiSorp white 384 plate at 20 μL/well and immobilized by being incubated overnight at 4° C. The human trkA solution was removed by reverse-centrifugation, Blocker Casein in TBS was added at 80 μL/well, and the plate was incubated for 30 min at room temperature. The plate was washed three times with a washing solution (TBS containing 0.05% Tween-20) to remove Blocker Casein in TBS. The rat femoral muscle homogenate, 5-fold diluted for a 0.3 mg/kg administration group and 50-fold diluted for a 3 mg/kg administration group with PBS containing 0.1% BSA, were each mixed with 0.4 μg/mL of biotinylated human NGF at equal amounts, and incubated for 30 min at room temperature, and the resulting samples were added at 20 μL/well. Since the collected muscle tissues were diluted with a tissue homogenate solution that is 2.5 times the amount of the muscle tissues, the antibody concentrations in the femoral muscle of the 0.3 mg/kg administration group and the 3 mg/kg administration group were evaluated by using solutions 35-fold and 350-fold diluted, respectively.

The biotinylated human NGF used herein was prepared by biotinylating human NGF (R&D Systems, 256-GF-100/CF) with EZ-Link NHS-PEG4-Biotin (Thermo Scientific, 21329). The biotinylation of human NGF was performed by adding 5 μL of 5 mM NHS-PEG4-Biotin solution to the 1 mL of 0.4 mg/mL, human NGF, incubating for 2 h on ice under a shaded condition, and exchanging the solution of the reaction mixture to PBS by using Amicon Ultra-0.5 mL 3K (Millipore, UFC500324) twice according to the manual.

PBS containing 0.1% BSA and 10 μg/mL of h1f.6 antibody diluted with PBS containing 0.1% BSA were prepared as the control. The control samples for the 0.3 mg/kg administration group and the 3 mg/kg administration group were diluted with PBS containing 0.1% BSA, which contains 10% and 1% of antibody-free femoral muscle homogenate, respectively. After the incubation for 30 min at room temperature, the plate was washed three times with the washing solution and 20 μL of 1,000-fold diluted alkaline phosphatase-labeled streptavidin (Thermo, 21324) in 20-fold diluted Blocking One in TBS containing 0.05% Tween-20 was added per well. After the incubation for 30 min at room temperature, the plate was washed three times with the washing solution and 20 μL of alkaline phosphatase substrate (Chemiluminescent AP Microwell/Membrane Substrate, Super Sensitive, 450 nm; SurModics, APU4-0100-01) mixed at 1:1 with 10-fold diluted solution of 200 mM Tris (pH 9.8) buffer containing 10 mM magnesium chloride was added per well. After the incubation for 30 mM at room temperature, the signal value was measured with the EnVision counter (Perkin Elmer).

To calculate the binding inhibition activity of antibody to human NGF at each concentration, the measured value of PBS containing 0.1% BSA was set to 0% and the measured value of 10 μg/mL of each antibody was set to 100%. The test was performed in duplicates (with 4 or 8 wells for control), and the arithmetic mean was obtained.

Consequently, the 0.3 mg/kg administration group showed a binding inhibition activity of 21.2% even in a condition where antibody concentration in femoral muscle is 35-fold diluted. Further, the 3 mg/kg administration group showed a binding inhibition activity of 59.9% in the condition where antibody concentration in femoral muscle is 350-fold diluted. It was confirmed that in femoral muscle tissues in the groups where h1f.6 antibody is administered at 0.3 mg/kg and 3 mg/kg, the antibody has binding inhibition activity against human NGF by inhibiting the binding between human NGF and its receptor trkA.

The above clearly demonstrates that the anti-human NGF antibody Fab fragment of the present invention, h1f.6 antibody, retains its antibody concentration at the target tissue and the binding activity to human NGF when it is locally administered, and thereby inhibits the binding between human NGF and its receptor. The anti-human NGF antibody Fab fragment of the present invention, h1f.6 antibody, holds a high potential for providing an excellent medicine that expresses desirable local drug effects at the target tissue for the less local dosage.

Example 8

Evaluation of Analgesic Effects in a Rat Postoperative Pain Model After Plantar Incision The analgesic effects of h1f.6 antibody on postoperative pain by local administration into the operated site were evaluated in a rat plantar incision model of postoperative pain (Banik R K et al. Pain 2005; 117. p. 68-76), which is considered to reflect the postoperative pain in clinical model. Patent Document 3 shows that systemic intravenous administration of the fully human anti-human NGF antibody 1-15 (N52D-A)-Fab'-10k PEG exhibits the analgesic effect in this model. In this study, 1-15 (N52D-A)-Fab'-10k PEG was used as a comparator on postoperative pain in local and systemic administration for the evaluation of the analgesic effects of local administration of h1f.6 antibody.

Specifically, five groups were assigned in total with each operation group consisting of 10 rats and each non-operation group consisting of 5 rats, the groups being a non-operation group, a solvent (20 mM Citrate, 120 mM NaCl, pH6) group, a group that was locally administered 900 μg of h1f.6 antibody to the plantar, a group that was locally administered 900 μg of 1-15 (N52D-A)-Fab'-10k PEG to the plantar, and a group that was administered 1 mg/kg of 1-15 (N52D-A)-Fab'-10k PEG intravenously. Local intraplantar administration was carried out by implanting approximately 2 mg piece of Spongel (registered trademark) sheet (Astellas Pharma), which was immersed and swelled by 30 μL of 30 mg/mL antibody solution, to the incised portion of the plantar muscle. In the solvent group and the group that was administered 1 mg/kg of 1-15 (N52D-A)-Fab'-10k PEG intravenously, they were implanted Spongel sheets which was immersed and swelled with solvents. In this evaluation, the plantar of the left hind paw was incised for about 10 mm length in a straight line starting from a point about 5 mm from the tip of the heel in the toe direction under anesthesia using isoflurane, and the exposed plantar muscle was incised vertically before returning the muscle to its position and implanting the Spongel sheet, then the muscle was mattress-sutured at two points using a nylon thread. The pain threshold was measured at 24 h, 48 h and 72 h after operation. The pain threshold was performed using Dynamic plantar aesthesiometer (Ugo Basile) to measure the pressure indicating the avoidance behavior against pressure to the rat's plantar.

The arithmetic mean of three pressure threshold values that caused an aversive behavior in the individual rats in each group was calculated as the pain threshold, and the improvement rate of the pain threshold of each group that was administered a pharmaceutical agent was calculated by setting the pain threshold of the non-operation group to 100%, and the pain threshold of the solvent group to 0%. As a result, 24 h after operation, the improvement rates of pain threshold in the group that was locally administered 900 μg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously were 34%, 49%, and 46%, respectively, and the pain threshold of each group that was administered a pharmaceutical agent showed a significant improvement with $p<0.05$ versus the solvent group with the Student-t test. Further, 48 h after operation, the improvement rates of pain threshold in the group that was locally administered 900 μg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously were 38%, 31%, and 34%, respectively, and the pain threshold in each group that was administered a pharmaceutical agent showed a significant improvement with $p<0.05$ versus the solvent group with the Student-t test. Further, 72 h after operation, the improvement rates of pain threshold in the group that was locally administered 900 μg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously were 26%, 33%, and 28%, respectively, and the pain threshold of each group that was administered a pharmaceutical agent showed a significant improvement with $p<0.05$ versus the solvent group in the Student-t test. When a Tukey's multiple comparison test was performed, no significant difference with $p<0.05$ was observed in the pain threshold in the three groups, namely, the group that was locally administered 900

μg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously, at any of 24 h, 48 h and 72 h after operation. This showed that the analgesic effects observed between these three groups are pharmacologically equal at 24 h, 48 h and 72 h after operation, respectively.

Example 9

Evaluation of Drug Concentration in Plasma or Tissue by Local Administration

To evaluate the concentration of each antibody in the plantar muscle or plasma in the evaluation of EXAMPLE 8, a group that was locally administered 900 μg of h1f.6 antibody to the plantar, a group that was locally administered 900 μg of 1-15 (N52D-A)-Fab'-10k PEG to the plantar, and a group that was administered 1 mg/kg of 1-15 (N52D-A)-Fab'-10k PEG intravenously were assigned in rats at n=3 by a method similar to EXAMPLE 8, and the antibody concentration in the plantar muscle and the plasma was measured 24 h after operation by electrochemiluminescence (ECL) assay. The local administration to the plantar was carried out similarly to EXAMPLE 8 by implanting approximately 2 mg piece of Spongel (registered trademark) sheet (Astellas Pharma), which is immersed and swelled by 30 μL of 30 mg/mL antibody solution, to the incised portion of the plantar muscle.

The antibody concentration in the plantar muscle was obtained by measuring the concentration of samples, which were homogenized with 9-fold volume of plantar tissue homogenate solution (10 mM Tris, 137 mM NaCl, 1% Triton X-100, 10% Glycerol, cOmplete, Mini (Roche), pH 8.0), and multiplying that the concentration by 10. Measurement with ECL assay was performed using two types of anti-1-15 antibodies, ANA-IBL-13A and biotinylated ANA-IBL-52A. In addition, the biotinylated ANA-IBL-52A is produced by biotinylation of ANA-IBL-52A following the technical manual for the Biotin Labeling Kit-NH2 (Dojindo Laboratories, LK03).

The ECL assay method is shown below. ANA-IBL-13A diluted with TBS to a concentration of 5,000 ng/mL was added to Multi-array 96-well Plate (Meso Scale Discovery, L15XA-3) at 25 μL/well. The plate was incubated for 1 h at room temperature to immobilize ANA-IBL-13A. The ANA-IBL-13A solution was removed by reverse-centrifugation, the plate was washed three times with a washing solution (TBS containing 0.05% Tween-20), and 150 μL of Blocker Casein in TBS (Thermo, 37532) was added per well. After the plate was incubated for 1 h at room temperature, Blocker Casein in TBS was removed by reverse-centrifugation. The plate was washed three times by the washing solution and 25 μL of 10-fold diluted plasma sample and plantar muscle homogenate with a diluent (Blocker Casein in TBS containing 0.05% Tween-20) was added per well. To create a calibration curve for the plasma sample, h1f.6 antibody and 1-15 (N52D-A)-Fab'-10k PEG diluted in 10 steps ranging from 333 ng/mL to 0.017 ng/mL with the diluent containing an antibody-free 10% plasma were prepared, and the diluent containing an antibody-free 10% plasma was prepared as the control. To create a calibration curve for plantar muscle homogenate, h1f.6 antibody and 1-15 (N52D-A)-Fab'-10k PEG diluted in 10 steps ranging from 333 ng/mL to 0.017 ng/mL with the diluent containing an antibody-free 10% of plantar muscle homogenate were prepared. The diluent containing an antibody-free 10% of plantar muscle homogenate was prepared as the control. After the plate was incubated for 1 h at room temperature, the solution was removed by reverse-centrifugation. The plate was washed three times with the washing solution, 25 μL of the biotinylated ANA-IBL-52A diluted to 1,000 ng/mL with the diluent was added per well, and the plate was incubated for 1 h at room temperature. The solution was removed by reverse-centrifugation, the plate was washed three times with the washing solution, and 25 μL of 500-fold diluted MSD SULFO-TAG labeled Streptavidin (Meso Scale Discovery, R32AD-1) with the diluent was added per well. The plate was incubated for 1 h at room temperature, the solution was removed by reverse-centrifugation, and the plate was washed three times with the washing solution. After 150 μL of MSD Read Buffer T (4×) (Meso Scale Discovery, R92TC-1) 2-fold diluted with ultrapure water (MilliQ (registered trademark), Merck) was added per well, the electrochemiluminescence of the mixture was measured using SECTOR Imager 6000 (Meso Scale Discovery).

A calibration curve was created to calculate the antibody concentration. The regression equation was analyzed using four or five parameter logistic curve fitting algorithm. Using the calibration curve, the antibody concentrations in the plasma and the plantar muscle were calculated for each point. Each test was performed in triplicates, and the arithmetic mean of the calculated concentrations was obtained. The limit of determination of h1f.6 antibody in this test was 0.2 ng/mL for concentration in plasma, and 2 ng/mL for concentration in plantar muscle, and the limit of determination of fully human anti-NGF antibody 1-15 (N52D-A)-Fab'-10k PEG was 0.5 ng/mL for concentration in plasma, and 2 ng/mL for concentration in plantar muscle.

The concentration in the plantar muscle of the group that was locally administered 900 μg of h1f.6 antibody to the plantar, the group that was locally administered 900 μg of 1-15 (N52D-A)-Fab'-10k PEG to the plantar, and the group that was intravenously administered 1 mg/kg of 1-15 (N52D-A)-Fab'-10k PEG at 24 hours after administration was 132 ng/mL, 46.2 ng/mL, and 24.1 ng/mL, respectively. The concentration in the plantar muscle was the highest for local administration of h1f.6 antibody to the plantar. On the other hand, the concentration in plasma at 24 hours after administration was less than 0.230 ng/mL (of the three examples one was 0.230 ng/mL, and two were less than 0.2 ng/mL), 65.1 ng/mL, 396 ng/mL, respectively, and the concentration in plasma was the lowest for local administration of h1f.6 antibody to the plantar.

Based on the concentration in the plantar muscle and the concentration in plasma of each antibody, the concentration ratios in the plantar muscle/plasma at 24 hours after administration were calculated for the group that was locally administered 900 μg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously. The concentration in plasma at 24 hours after administration for individuals that were administered 900 μg of h1f.6 antibody to the plantar was assigned the value of limit of determination, 0.2 ng/mL, as it was below limit of determination in this condition.

The concentration ratios in the plantar muscle/plasma at 24 hours after administration for the group that was locally administered 900 mg of h1f.6 antibody to the plantar, the group that was locally administered 900 μg of 1-15 (N52D-A)-Fab'-10k PEG to the plantar, and the group that was administered 1 mg/kg of 1-15 (N52D-A)-Fab'-10k PEG intravenously were 628, 0.71, and 0.061, respectively. The concentration ratio of plantar muscle/plasma for 1-15 (N52D-A)-Fab'-10k PEG administered to the plantar was more 10 times higher than that for intravenous administration. The h1f.6 antibody exhibited more than 800 times higher plantar muscle/plasma concentration ratio than 1-15 (N52D-A)-Fab'-10k PEG, when they compared by local administration to plantar.

The above results indicate that a local administration of h1f.6 antibody which is an anti-human NGF antibody Fab fragment of the present invention can reduce drug concentration in the systemic blood flow while it can maintain the drug concentration at the target local area, and further demonstrate that it reduces drug concentration in the systemic blood flow while it maintains the drug concentration at the target local area more effectively than fully human anti-human NGF antibody 1-15 (N52D-A)-Fab?-10k PEG. As such, the anti-human NGF antibody Fab fragment of the present invention, holds a high potential for providing an excellent medicine that reduces systemic side effects while it expresses desirable drug effects at a local area.

INDUSTRIAL APPLICABILITY

The anti-human NGF antibody Fab fragment of the present invention is expected to be useful in the treatment of postoperative pain. The anti-human NGF antibody Fab fragment of the present invention is expected to be particularly useful as a superior pharmaceutical agent that reduces systemic side effects from exposure in blood while expressing desirable drug effects at a local area.

FREE TEXT OF SEQUENCE LISTING

Explanations are provided for "Artificial Sequence" described for each numerical index <223> of the sequence listing shown below. Specifically, the base sequence shown by SEQ ID NO:1 of the sequence listing is the base sequence of the heavy-chain fragment of h1f.6 antibody, and the amino acid sequence shown by SEQ ID NO:5 of the sequence listing is the amino acid sequence of the heavy-chain fragment encoded by SEQ ID NO:1. The base sequence shown by SEQ ID NO:2 of the sequence listing is the base sequence of the heavy-chain fragment of h1f.7 antibody, and the amino acid sequence shown by SEQ ID NO:6 of the sequence listing is the amino acid sequence of the heavy-chain fragment encoded by SEQ ID NO:2. The base sequence shown by SEQ ID NO:3 of the sequence listing is the base sequence of the heavy-chain fragment of h1f8 antibody, and the amino acid sequence shown by SEQ ID NO:7 of the sequence listing is the amino acid sequence of the heavy-chain fragment encoded by SEQ ID NO:3. The base sequence shown by SEQ ID NO:4 of the sequence listing is the base sequence of the light-chain of 1-15(N52D-A)-Fab' fragment, and the amino acid sequence shown by SEQ ID NO:8 of the sequence listing is the amino acid sequence of the light-chain encoded by SEQ ID NO:4. The base sequence shown by SEQ ID NO:9 of the sequence listing is the base sequence of the heavy-chain variable region of the anti-human NGF antibody Fab fragment of the present invention, and the amino acid sequence shown by SEQ ID NO:10 of the sequence listing is the amino acid sequence of the heavy-chain variable region encoded by SEQ ID NO:9. The base sequence shown by SEQ ID NO:11 of the sequence listing is the base sequence of the light-chain variable region of the anti-human NGF antibody Fab fragment of the present invention, and the amino acid sequence shown by SEQ ID NO:12 of the sequence listing is the amino acid sequence of the light-chain variable region encoded by SEQ ID NO:11.

The invention claimed is:
1. An anti-human NGF antibody Fab fragment selected from the group consisting of (a) and (b):
   (a) an anti-human NGF antibody Fab fragment consisting of a heavy-chain fragment consisting of the amino acid sequence of SEQ ID NO: 5 and a light-chain consisting of the amino acid sequence of SEQ ID NO: 8; and
   (b) an anti-human NGF antibody Fab fragment, consisting of a heavy-chain fragment consisting of the amino acid sequence of SEQ ID NO: 5, where a glutamine at amino acid position 1 of SEQ ID NO:5 is modified to a pyroglutamic acid, and a light-chain fragment consisting of the amino acid sequence of SEQ ID NO: 8.

2. The anti-human NGF antibody Fab fragment according to claim 1, consisting of a heavy-chain fragment consisting of the amino acid sequence of SEQ ID NO: 5 and a light-chain fragment consisting of the amino acid sequence of SEQ ID NO: 8.

3. The anti-human NGF antibody Fab fragment according to claim 1, consisting of a heavy-chain fragment consisting of the amino acid sequence of SEQ ID NO: 5, where a glutamine at amino acid position 1 of SEQ ID NO: 5 is modified to a pyroglutamic acid, and a light-chain fragment consisting of the amino acid sequence of SEQ ID NO: 8.

4. A pharmaceutical composition comprising the anti human NGF antibody Fab fragment according to claim 1, and a pharmaceutically acceptable carrier.

5. The pharmaceutical composition according to claim 4, wherein the pharmaceutical composition is for local administration and for treating postoperative pain related to NGF.

6. A pharmaceutical composition, comprising:
   (a) the anti-human NGF antibody Fab fragment according to claim 1;
   (b) the anti-human NGF antibody lab fragment comprising a heavy-chain fragment consisting of the amino acid sequence of SEQ ID NO: 5, where a glutamine at amino acid position 1 of SEQ ID NO: 5 is modified to a pyroglutamic acid, and a light-chain fragment consisting of the amino acid sequence of SEQ ID NO: 8 according to claim 1; and
   (c) a pharmaceutically acceptable carrier.

7. The pharmaceutical composition according to claim 6, wherein the pharmaceutical composition is for local administration and for treating postoperative pain related to NGF.

8. An isolated polynucleotide molecule comprising a polynucleotide encoding the heavy-chain fragment of the anti-human NGF antibody Fab fragment of claim 1, consisting of the amino acid sequence of SEQ ID NO: 5, and a polynucleotide encoding the light-chain of the anti-human NGF antibody Fab fragment of claim 1, consisting of the amino acid sequence of SEQ ID NO: 8.

9. An expression vector selected from the group consisting of (a) and (b):
   (a) an expression vector comprising a polynucleotide encoding the heavy-chain fragment of the anti-human NGF antibody Fab fragment of claim 1, consisting of the amino acid sequence of SEQ ID NO: 5, and a polynucleotide encoding the light-chain of the anti-human NGF antibody Fab fragment of claim 1, consisting of the amino acid sequence of SEQ ID NO: 8; and
   (b) an expression vector comprising a polynucleotide encoding the heavy-chain fragment of the anti-human NGF antibody Fab fragment of claim 1, consisting of the amino acid sequence of SEQ ID NO: 5, and an expression vector comprising a polynucleotide encoding the light-chain of the anti-human NGF antibody Fab fragment of claim 1, consisting of the amino acid sequence of SEQ ID NO: 8.

10. An isolated host cell transformed with the expression vector according to claim 9.

11. The host cell according to claim 10, wherein the host cell is selected from the group consisting of (a) and (b):
   (a) the host cell transformed with the expression vector comprising the polynucleotide encoding the heavy-chain fragment of the anti-human NGF antibody Fab fragment, consisting of the amino acid sequence of SEQ ID NO: 5, and the polynucleotide encoding the light-chain of the anti-human NGF antibody Fab fragment, consisting of the amino acid sequence of SEQ ID NO: 8; and
   (b) the host cell-transformed with an expression vector comprising the polynucleotide encoding the heavy-chain fragment of the anti-human NGF antibody Fab fragment, consisting of the amino acid sequence of SEQ ID NO: 5, and with an expression vector comprising the polynucleotide encoding the light-chain of the anti-human NGF antibody Fab fragment consisting of the amino acid sequence of SEQ ID NO: 8.

12. The host cell according to claim 11, wherein the host cell is transformed with the expression vector comprising the polynucleotide encoding the heavy-chain fragment consisting of the amino acid sequence of SEQ ID NO: 5, and the expression vector comprising the polynucleotide encoding the light-chain consisting of the amino acid sequence of SEQ ID NO: 8 .

13. A method for producing an anti-human NGF antibody Fab fragment, comprising culturing the host cell according to claim 11 to express the anti-human NGF antibody Fab fragment, and thereby producing and isolating the anti-human NGF antibody Fab fragment.

14. An anti-human NGF antibody Fab fragment produced by the method according to claim 13.

15. A method for treating postoperative pain related to NGF, comprising locally administering an effective amount of the anti-human NG antibody Fab fragment according to claim 1 to a subject in need thereof, thereby alleviating the postoperative pain related to NGF.

* * * * *

SEQUENCE LISTING

```
<160> NUMBER OF SEQ ID NOS: 12

<210> SEQ ID NO 1
<211> LENGTH: 675
<212> TYPE: DNA
<213> ORGANISM: Artificial Sequence
<220> FEATURE:
<223> OTHER INFORMATION: DNA encoding h1f.6 heavy chain fragment

<400> SEQUENCE: 1
caggtgcagc tacagcagtg gggcgcagga ctgttgaagc cttcggagac cctgtccctc      60
acctgcgctg tctatggtgg gtccttcagt ggttactact ggagctgggt ccgccagccc     120
ccagggaagg ggctggagtg gattgggaa atcgaccata gtggaagcac caacaacaac      180
ccgtccctca agagtcgagt caccatatca gtaggcacgt ccaagaacca gttctccctg     240
aagctgagct ctgtgaccgc cgcggacacg gctgtgtatt actgttcgag agatgggggc     300
cccgaatcgg ggatgggggc ttttgatatc tggggccaag ggacaatggt caccgtctcc     360
tcagcctcca ccaagggccc atcggtcttc cccctggcac cctcctccaa gagcacctct     420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actcccttag tagcgtggtg accgtgccc ccagcagctt gggcacccag      600
acctacatct gcaacgtgaa tcacaagccc agcaacacca aggtggacaa gaaagttgag     660
```

```
cccaaatctt gtgac                                                     675
```

```
<210> SEQ ID NO 2
<211> LENGTH: 672
<212> TYPE: DNA
<213> ORGANISM: Artificial Sequence
<220> FEATURE:
<223> OTHER INFORMATION: DNA encoding h1f.7 heavy chain fragment

<400> SEQUENCE: 2
caggtgcagc tacagcagtg gggcgcagga ctgttgaagc cttcggagac cctgtccctc    60
acctgcgctg tctatggtgg gtccttcagt ggttactact ggagctgggt ccgccagccc   120
ccagggaagg ggctggagtg gattggggaa atcgaccata gtggaagcac caacaacaac   180
ccgtccctca agagtcgagt caccatatca gtaggcacgt ccaagaacca gttctccctg   240
aagctgagct ctgtgaccgc cgcggacacg gctgtgtatt actgttcgag agatgggggc   300
cccgaatcgg ggatggggc ttttgatatc tggggccaag gacaatggt caccgtctcc    360 tcagcctcca ccaagggccc atcggtcttc cccctggcac cctcctccaa gagcacctct   420
gggggcacag cggccctggg ctgcctggtc aaggactact ccccgaacc ggtgacggtg    480 tcgtggaact caggcgccct gaccagcggc gtgcacacct tcccggctgt cctacagtcc   540
tcaggactct actcccttag tagcgtggtg accgtgccct ccagcagctt gggcacccag   600
acctacatct gcaacgtgaa tcacaagccc agcaacacca aggtggacaa gaaagttgag   660
cccaaatctt gt                                                        672
```

```
<210> SEQ ID NO 3
<211> LENGTH: 678
<212> TYPE: DNA
<213> ORGANISM: Artificial Sequence
<220> FEATURE:
<223> OTHER INFORMATION: DNA encoding h1f.8 heavy chain fragment

<400> SEQUENCE: 3
caggtgcagc tacagcagtg gggcgcagga ctgttgaagc cttcggagac cctgtccctc    60
acctgcgctg tctatggtgg gtccttcagt ggttactact ggagctgggt ccgccagccc   120
ccagggaagg ggctggagtg gattggggaa atcgaccata gtggaagcac caacaacaac   180
ccgtccctca agagtcgagt caccatatca gtaggcacgt ccaagaacca gttctccctg   240
aagctgagct ctgtgaccgc cgcggacacg gctgtgtatt actgttcgag agatgggggc   300
cccgaatcgg ggatggggc ttttgatatc tggggccaag gacaatggt caccgtctcc    360 tcagcctcca ccaagggccc atcggtcttc cccctggcac cctcctccaa gagcacctct   420
gggggcacag cggccctggg ctgcctggtc aaggactact ccccgaacc ggtgacggtg    480 tcgtggaact caggcgccct gaccagcggc gtgcacacct tcccggctgt cctacagtcc   540
tcaggactct actcccttag tagcgtggtg accgtgccct ccagcagctt gggcacccag   600
acctacatct gcaacgtgaa tcacaagccc agcaacacca aggtggacaa gaaagttgag   660
cccaaatctt gtgcagcc                                                 678
```

```
<210> SEQ ID NO 4
<211> LENGTH: 657
<212> TYPE: DNA
<213> ORGANISM: Artificial Sequence
<220> FEATURE:
<223> OTHER INFORMATION: DNA encoding 1-15(N52D-A)-Fab?ffragment light
      chain
```

<400> SEQUENCE: 4

```
gatattgtga tgactcagtc tccactctcc ctgcccgtca cccctggaga gccggcctcc    60
atctcctgca ggtctagtca gagcctcctg catagtaatg gattcaacta tttgggttgg   120
tacctgcaga agccagggca gtctccacag ctcctgatct atttgggttc taatcgggcc   180
tccggggtcc ctgacaggtt cagtggcagt ggatcaggca cagattttac tctgaaaatc   240
agcagagtgg aggctgagga tgttgggggtt tattactgca tgcaagctct acaaactccg   300
tacactttg gccaggggac caagctggag atcaaacgga ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 5
<211> LENGTH: 225
<212> TYPE: PRT
<213> ORGANISM: Artificial Sequence
<220> FEATURE:
<223> OTHER INFORMATION: h1f.6 heavy chain fragment

<400> SEQUENCE: 5

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Val Arg Gln Pro Pro Gly Lys Gly Leu Glu Trp Ile
         35                  40                  45

Gly Glu Ile Asp His Ser Gly Ser Thr Asn Asn Asn Pro Ser Leu Lys
     50                  55                  60

Ser Arg Val Thr Ile Ser Val Gly Thr Ser Lys Asn Gln Phe Ser Leu
 65                  70                  75                  80

Lys Leu Ser Ser Val Thr Ala Ala Asp Thr Ala Val Tyr Tyr Cys Ser
                 85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp
225
```

```
<210> SEQ ID NO 6
<211> LENGTH: 224
<212> TYPE: PRT
<213> ORGANISM: Artificial Sequence
<220> FEATURE:
<223> OTHER INFORMATION: h1f.7 heavy chain fragment

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

<210> SEQ ID NO 7
<211> LENGTH: 226
<212> TYPE: PRT
<213> ORGANISM: Artificial Sequence
<220> FEATURE:
<223> OTHER INFORMATION: h1f.8 heavy chain fragment

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95
```

Arg Asp Gly Gly Pro Glu Ser Gly Met Gly Ala Phe Asp Ile Trp Gly
            100                 105                 110

Gln Gly Thr Met Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Ala Ala
225

<210> SEQ ID NO 8
<211> LENGTH: 219
<212> TYPE: PRT
<213> ORGANISM: Artificial Sequence
<220> FEATURE:
<223> OTHER INFORMATION: 1-15(N52D-A)-Fab?ffragment light chain

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Gly Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 363
<212> TYPE: DNA
<213> ORGANISM: Artificial Sequence
<220> FEATURE:
<223> OTHER INFORMATION: VH gene of anti-human NGF antibody
<220> FEATURE:
<221> NAME/KEY: CDS
<222> LOCATION: (1)..(363)

<400> SEQUENCE: 9

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
            20                  25                  30 tac tgg agc tgg gtc cgc cag ccc cca ggg aag ggg ctg gag tgg att     144
Tyr Trp Ser Trp Val Arg Gln Pro Pro Gly Lys Gly Leu Glu Trp Ile
        35                  40                  45 ggg gaa atc gac cat agt gga agc acc aac aac aac ccg tcc ctc aag     192
Gly Glu Ile Asp His Ser Gly Ser Thr Asn Asn Asn Pro Ser Leu Lys
    50                  55                  60 agt cga gtc acc ata tca gta ggc acg tcc aag aac cag ttc tcc ctg     240
Ser Arg Val Thr Ile Ser Val Gly Thr Ser Lys Asn Gln Phe Ser Leu
65                  70                  75                  80 aag ctg agc tct gtg acc gcc gcg gac acg gct gtg tat tac tgt tcg     288
Lys Leu Ser Ser Val Thr Ala Ala Asp Thr Ala Val Tyr Tyr Cys Ser
                85                  90                  95 aga gat ggg ggc ccc gaa tcg ggg atg ggg gct ttt gat atc tgg ggc     336
Arg Asp Gly Gly Pro Glu Ser Gly Met Gly Ala Phe Asp Ile Trp Gly
            100                 105                 110 caa ggg aca atg gtc acc gtc tcc tca                                 363
Gln Gly Thr Met Val Thr Val Ser Ser
        115                 120
```

<210> SEQ ID NO 10
<211> LENGTH: 121
<212> TYPE: PRT
<213> ORGANISM: Artificial Sequence
<220> FEATURE:
<223> OTHER INFORMATION: Synthetic Construct

<400> SEQUENCE: 10

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser
        115                 120
```

<210> SEQ ID NO 11
<211> LENGTH: 339
<212> TYPE: DNA
<213> ORGANISM: Artificial Sequence
<220> FEATURE:
<223> OTHER INFORMATION: VL gene of anti-human NGF antibody
<220> FEATURE:
<221> NAME/KEY: CDS
<222> LOCATION: (1)..(339)

<400> SEQUENCE: 11

```
gat att gtg atg act cag tct cca ctc tcc ctg ccc gtc acc cct gga      48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga ttc aac tat ttg ggt tgg tac ctg cag aag cca ggg cag tct     144
Asn Gly Phe Asn Tyr Leu Gly Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt act ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg tac act ttt ggc cag ggg acc aag ctg gag atc aaa     336
Leu Gln Thr Pro Tyr Thr Phe Gly Gln Gly Thr Lys Leu Glu Ile Lys
            100                 105                 110 cgg                                                                  339
Arg
```

<210> SEQ ID NO 12
<211> LENGTH: 113
<212> TYPE: PRT
<213> ORGANISM: Artificial Sequence
<220> FEATURE:
<223> OTHER INFORMATION: Synthetic Construct

<400> SEQUENCE: 12

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Gly Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg
```